| United States Patent [19] | [11] | 4,256,653 |
|---|---|---|
| Atkinson | [45] | Mar. 17, 1981 |

[54] PREPARATION AND USE OF HIGH SURFACE AREA TRANSITION METAL CATALYSTS

[75] Inventor: Gary B. Atkinson, Reno, Nev.

[73] Assignee: The United States of America as represented by the Secretary of the Interior, Washington, D.C.

[21] Appl. No.: 801,442

[22] Filed: May 27, 1977

Related U.S. Application Data

[62] Division of Ser. No. 738,201, Nov. 3, 1976, Pat. No. 4,071,473.

[51] Int. Cl.$^3$ .................................................. C07C 1/04
[52] U.S. Cl. ............................................ 260/449.6 M
[58] Field of Search ................ 260/449.6 R, 449.6 M, 260/449 M

[56] References Cited

U.S. PATENT DOCUMENTS

| 2,183,146 | 12/1939 | Michael | 260/449.6 |
|---|---|---|---|
| 2,445,796 | 7/1948 | Millendorf | 260/449 R |
| 2,593,250 | 4/1952 | Black | 260/449.6 |
| 2,686,819 | 8/1954 | Johnson | 260/449 M |
| 3,361,535 | 1/1968 | Pollitzer et al. | 260/449 M |

*Primary Examiner*—Howard T. Mars
*Attorney, Agent, or Firm*—William S. Brown; Donald A. Gardiner

[57] ABSTRACT

Highly active catalysts, suitable for use in hydrogenation and other reactions, are prepared from an alloy of one or more of the Group VIII transition metals with yttrium or a rare earth metal. The alloy is ground to the desired particle size and is thereafter reacted with a gas containing carbon monoxide and hydrogen to form an intimate physical admixture of the Group VIII metal or its corresponding carbide with the oxide of yttrium or the rare earth metal.

5 Claims, 2 Drawing Figures

PREPARATION AND USE OF HIGH SURFACE AREA TRANSITION METAL CATALYSTS

This is a division of application Ser. No. 738,201 filed Nov. 3, 1976, now U.S. Pat. No. 4,071,473.

BACKGROUND OF THE INVENTION

This invention relates generally to manufacture and activation of metal-containing catalysts and their use in hydrocarbon conversion reactions. More particularly, this invention concerns a method for making and activating a metal or metal carbide—metal oxide catalyst especially useful for promoting hydrogenation reactions in general and the methanation reaction in particular.

The transition metals of Group VIII of the Periodic Table have long been known for their catalytic activity when prepared in a finely divided or high surface area form. Nickel in particular has found extensive use as a catalyst in hydrogeneration and methanation reactions. A number of standard techniques to obtain high surface area metal catalysts have been developed. Illustrative of these are impregnation, precipitation, ion-exchange, Raney metal and reduction of the fused oxide. Since reactions which are promoted with a catalyst usually occur on the surface of the catalyst through adsorption of one or more of the reactants, it is usually desirable to obtain catalysts with the largest active surface area practicable.

When impregnation techniques are used to prepare a catalyst, a compound which is usually a salt of the desired catalytic elements is dissolved in a liquid. A high surface area support material such as kieselguhr, alumina, or activated charcoal is wetted with the solution and the mixture is thereafter dried and calcined. If a catalytic element in its metallic state is desired, the calcined mixture is thereafter reduced using a gaseous reductant such as hydrogen. Boyd et al in U.S. Pat. No. 2,666,756 disclose impregnation techniques for the preparation of metallic nickel or cobalt catalysts promoted with other compounds including the oxides of cerium and thorium supported on Kieselguhr and silica gel. Their catalyst finds use for the polymerization of ethylene.

Catalysts may be prepared by precipitation techniques in which a catalytic metal is precipitated from solution, generally as the hydroxide, either alone or with a carrier compound. The resulting precipitate is washed and dried and the metal compound is thereafer reduced to elemental form. Very small catalyst particles having a large surface are produced by this technique.

Taylor et al, in U.S. Pat. Nos. 3,395,104 and 3,404,100 disclose catalysts prepared by coprecipitating nickel and alumina. The precipitated mixture was thereafter impregnated with a solution containing either a rare earth metal or yttrium and the resulting mixture was dried and calcined. After reduction with hydrogen, the catalyst was used to react steam with naphtha vapors to produce a methane-rich gas.

Catalysts may be prepared by ion-exchange with a high surface area support having a large number of protonic sites. A solution containing cationic metal is added to a stirred slurry of the support material in a liquid to effect ion-exchange at the protonic sites. Thereafter, the support is washed and dried and the exchanged metal may be reduced. This results in metallic sites dispersed over the large surface of the support.

A skeletal high surface transition metal catalyst may be prepared through the use of Raney alloys. An alloy is obtained by melting a transition metal such as iron, cobalt or nickel with a soluble metal such as aluminum or zinc. The cooled alloy is comminuted to a convenient particle size and then leached in a heated alkaline solution to dissolve the aluminum or zinc. The resulting catalyst has a large skeletal surface area of active metal and finds use in hydrogenation and methanation reactions.

Another technique for preparing catalysts is by reduction of a fused oxide. An oxide of an easily reducible metal is fused with a promoter or support material which may comprise an oxide of a difficulty reducible metal. The cooled material is ground, sized, and reduced with hydrogen at temperatures sufficiently low to prevent sintering. There is obtained a porous bulk material having a high surface area interlaced with oxide promoters.

While all of these techniques produce useful and active catalysts, no one of the prior art methods combines the advantages of high surface area, ease of preparation and activation, high specific reactivity and overall economy as do the catalysts of this invention.

SUMMARY OF THE INVENTION

A high surface area active catalyst is formed by reacting an alloy with a reactive gas mixture to oxidize one of the alloy components while leaving other alloy components in the metallic state. The alloy comprises one or more of the transition metals of Group VIII of the Periodic Table with one or more metals selected from the group consisting of yttrium and the rare earths. Formation of the catalyst is accomplished by reaction of the alloy with a reactive gas containing both carbon monoxide and hydrogen. At temperatures above about 300° C., this gas mixture reacts with yttrium and the rare earths contained in the alloy to form an intimate dispersion of the transition metal with oxides of the yttrium or rare earths.

While a treatment of the alloy with the reactive gas at temperatures above about 300° C. results in an active and useful catalyst, further surface area development can be attained in a second, activation step. This activation step comprises further treatment with the same gas but at a reduced temperature, i.e., below about 275° C. and preferably below 250° C. The resulting catalysts are useful in hydrogenation reactions in general and in the methanation reaction in particular.

DETAILED DESCRIPTION OF THE INVENTION

Figure 1:
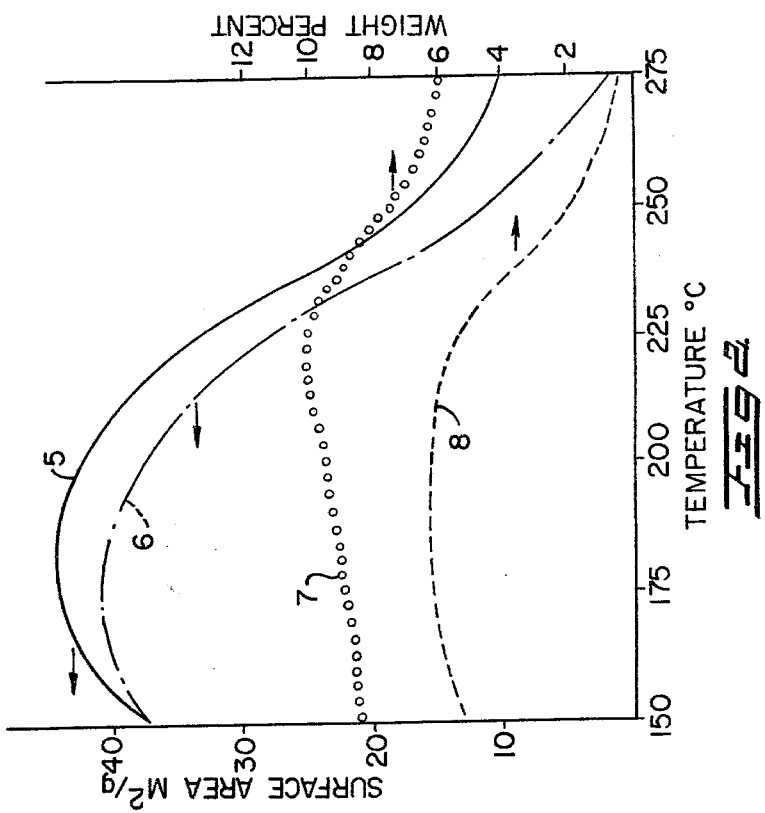
FIG. 1 is a graphical presentation of catalyst properties resulting from the initial catalyst preparation step.
Figure 2:
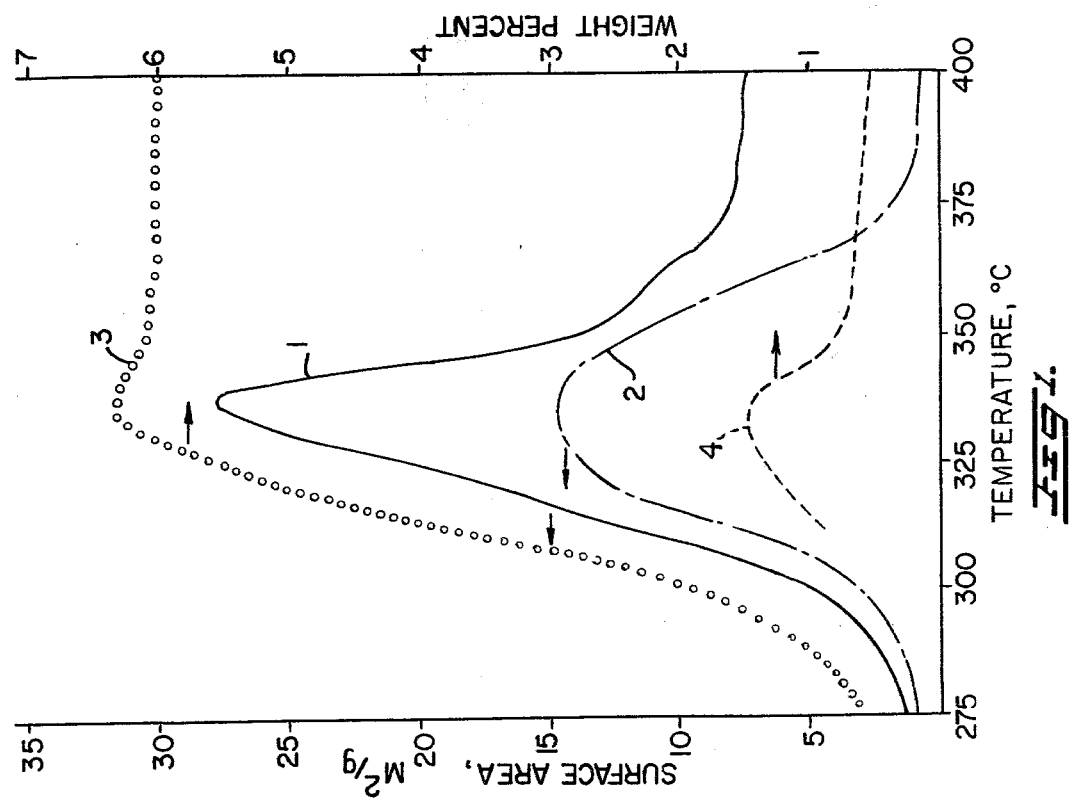
FIG. 2 illustrates changes in catalyst properties resulting from the second, activation step.

It has been found that novel, highly active catalysts can be produced by reaction of particular metal alloys with a gas mixture containing both carbon monoxide and hydrogen. The alloys contain a first component which may be any one of the transition metals of Group VIII of the Periodic Table or mixtures of these with a second component which may be any one of the rare earth metals, yttrium or mixtures of these. Alloy composition is not critical; a broad range of the two components can be used to produce useful catalysts. Alloy composition may usefully range from 5% to about 95% by weight of the first component metal with the balance being made up of the second component metal. More preferred compositions range from about 10% to about 80% by weight of the first component material. Nickel is preferred as the first component metal.

The alloy may be formed by fusion of the two metal components in the desired proportions under an inert atmosphere. Arc melting the alloy components on a water cooled copper hearth in a helium atmosphere is a convenient and entirely satisfactory method for forming the alloy. After the alloy is formed, it is cooled, preferably under an inert atmosphere, and then is comminuted to a convenient particle size. Since the alloys of interest are brittle, comminution may be accomplished using conventional crushing and grinding techniques.

Any one of the Group VIII transition metals, iron, cobalt, or nickel, may be used as the first alloy component, but nickel is preferred because of its generally higher catalytic activity. These metals may be also used in combination to make up the first component. Any one of the rare earth metals or yttrium may be used as the second component of the alloy system, but here a mixture of rare earth metals such as mischmetal is preferred because of economy. Mischmetal is a commercial form of mixed rare earth metal of indefinite composition but usually containing a major amount of cerium with lesser amounts of lanthanum, neodymium, praseodymium, and other rare earth metals. Because of the chemical similarity of the rare earths and yttrium, the precise composition of the second alloy component tends not to significantly affect catalyst properties. However, particularly high surface area catalysts are obtainable when using cerium alone as the second alloy component.

The reactive gas used to form and activate the catalyst must contain both hydrogen and carbon monoxide. It may be a mixture containing only hydrogen and carbon monoxide or it may be in admixture with other gases, including steam, carbon dioxide, lower hydrocarbons such as methane and similar gases. Inert diluent gases such as helium may also be used in the gas mixture. When the catalyst is to be used in methanation reactions, synthesis gas is preferred as the activating agent as it is readily available and produces entirely satisfactory results.

Initial catalyst formation is accomplished by reacting the alloy particles with the gas mixture at temperatures sufficiently high to oxidize the second alloy component. Oxidation is initiated at temperatures of about 300° C. Much higher temperatures can be used but little advantage is gained at temperatures above about 600° C. Suitable pressures may range from ambient to about 10 atmospheres, with ambient pressure being preferred when the subsequent activation step is not employed. Reaction is continued until substantially all of the second alloy component has been oxidized. The time required to complete oxidation is dependent upon temperature, upon reactive gas composition and upon gas flow rate, but is generally in the range of 1 to 24 hours. At the end of the oxidation step, the product displays useful catalytic properties and may be used to promote hydrogenation, methanation, and like reactions. Surface area of the catalyst at this stage is generally below about 30 $m^2/g$ as determined by the BET method and the active surface area is generally below about 10 $m^2/g$ as determined by CO adsorption.

Both BET surface area and active surface area can be substantially increased by subjecting the catalyst to a subsequent activation step. This step comprises contacting the catalyst with the same reactive gas mixture but at a lower temperature and higher pressure for a time sufficient for the catalyst to reach an equilibrium state. Temperatures employed in this step must be below about 275° C., and preferably below about 250° C., with pressures being above about 5 atmospheres, and preferably about 10 atmospheres. Use of elevated pressure in this activation step is generally necessary to avoid carbon deposition. In addition, use of similar elevated pressures in the initial catalyst formation step is preferred when the subsequent activation step is to be employed. Contacting time is dependent upon temperature and other variables, but again, is in the general range of 1 to 24 hours. Care should be taken to avoid too low temperatures in the activation step when nickel is present as the first alloy component so as to avoid any substantial production of nickel carbonyl. Minor losses of nickel as the carbonyl can be tolerated provided that proper precautions are taken to dispose of the gas. At the end of the activation step, the catalyst will typically display a BET surface area of 40 to 50 $m^2/g$ and an active surface area as determined by CO adsorption of about 40 $m^2/g$.

X-Ray diffraction and chemical analyses performed on the product of the initial catalyst-formation step indicate that the second alloy component is converted to the oxide form while the first alloy component remains in the metallic state. Similar analyses performed on the product of the activation step indicate that much of the transition metal is converted to the corresponding metal carbide.

The catalyst, either as initially formed or following activation, is stable if cooled to room temperature under an atmosphere of either the reactive gas or an inert gas. It is stable in air, can be handled and stored without hazard, and used in a chemical reaction without further treatment. However, if the catalyst is de-gassed, as by heating in vacuum, it becomes pyrophoric.

Reactions catalysed by the catalyst of the invention include hydrogenation reactions in general such as the hydrogenation of unsaturated hydrocargons, alcohols, and the like. The catalyst is particularly useful for promoting the methanation reaction which is the reaction of carbon monoxide and hydrogen to produce methane and water vapor. Testing of the catalyst in the methanation reaction has indicated that the turnover number is as much as ten times that of a commercial hydrogenation catalyst. Turnover number is a calculated value representing the number of molecules of methane formed per active catalyst site per second. Reaction conditions appropriate for use with the catalyst of this invention are essentially those of the prior art. Methanation, for example, may be accomplished at temperatures in the range of about 350° C. to 400° C., and at pressures ranging from about 1 to more than 100 atmospheres.

Details on the preferred methods for preparing, activating, testing, and using the catalysts of this invention are given in the following examples.

EXAMPLE 1

An alloy containing 32.3 wt-pct cerium and 67.7 wt-pct nickel, which conforms to the formula $CeNi_5$, was prepared by arc melting the metals on a water cooled copper hearth in a helium atmosphere. The cooled alloy was ground to a size range of $-25 +80$ mesh and samples were sequentially loaded into a stainless steel tube reactor. Successive samples were then reacted overnight with a flowing gas stream containing about 75% hydrogen and 25% carbon monoxide at 1 atmosphere total pressure and temperatures ranging from 275° C. to 400° C.

At the end of the reaction period, each sample was cooled to room temperature and subjected to analysis. Surface area was determined by the BET method and active surface area was determined by carbon monoxide adsorption. Chemical analyses for oxygen and carbon were also performed. The results of these tests are presented as FIG. 1.

In that FIG., curve 1 represents BET surface area, while curve 2 represents active surface area as determined by carbon monoxide adsorption. Curve 3 indicated oxygen content of the catalyst while curve 4 represents carbon content. As may be seen from the curves, development of total and active surface area paralleled oxidation of the cerium component reaching a maximum at a temperature of about 335° C. Reaction at higher temperatures achieved essentially complete oxidation of the cerium component of the alloy but both total and active surface area decreased with increasing temperature. Carbon content of the catalyst, present mainly as nickel carbide, peaked with the surface area and thereafter declined somewhat to an equilibrium value.

All of the fully oxidized catalysts were active for promoting the methanation reaction and may be used for that purposes without further surface area development obtained in the activation then those displaying the higher surface areas are preferred. Temperature of catalyst formation had little if any effect on the surface area obtained in the activation step provided that essentially complete oxidation of second alloy component was obtained in the formation step.

EXAMPLE 2

An alloy composition identical to that of Example 1 was subjected to an initial catalyst formation by reaction overnight with a flowing gas stream containing about 75% hydrogen and 25% carbon monoxide at 10 atmospheres total pressure, and a temperature of 350° C. Samples of the resulting catalysts were subjected to an activation step using the same gas mixture, reaction time, and pressure, but lower temperatures. The reacted samples were then cooled and subjected to analysis as in Example 1. Results of these analyses for BET surface area, active surface area, oxygen content and carbon content at temperatures ranging from 150° C. to 275° C. are presented as FIG. 1.

In that figure, curve 5 represents BET surface area while curve 5 represents active surface area as determined by carbon monoxide adsorption. Oxygen content as depicted by curve 7 and carbon content, represented by curve 8, were determined by chemical analysis. Both BET and active surface area generally increased ac activation temperature decreased, reaching maximum values at temperatures in the range of about 165° C. to about 210° C. Some decrease in surface area was noted at an activation temperature of 150° C. This decrease may be related to reaction of the nickel component with carbon monoxide to form nickel carbonyl as some production of nickel carbonyl was observed at the lower temperatures.

Oxygen content of the activated catalysts remained relatively constant over the entire temperature range while carbon content increased and then stabilized at temperatures below about 225° C. X-Ray diffraction analyses determined that the carbon was present in the form of nickel carbide. All of the catalyst samples were found to be highly active in promoting the methanation reaction.

EXAMPLE 3

A series of alloy compositions containing nickel as the first alloy component and mischmetal (MM) as the second component were prepared by arc melting the constituents on a water cooled copper hearth under a helium atmosphere. An approximate analysis of the MM showed 67 wt-pct Ce, 13 wt-pct La, 9 wt-pct Pr and 11 wt-pct Nd. The cooled alloys were ground and sized and catalysts were formed and activated as in Example 2.

Surface area of each catalyst composition was determined both by the BET method and by carbon monoxide adsorption and these values were compared to a commercial nickel hydrogenation catalyst sold under the designation Harshaw #0302T. In addition, the specific activity of each catalyst sample was determined and compared to that of the commercial catalyst. Specific activity was reported as the Turnover Number which is a calculated value representing the number of methane molecules formed on each catalyst site per second. Results obtained in these experiments are summarized in the following table:

TABLE 1

| Catalyst | BET Area $m^2/g$ | Active Area $m^2/g$ | Turnover No. @ 275° C. × $10^3$ |
|---|---|---|---|
| Harshaw #0302T | 77.6 | 14.3 | 13 |
| 10 wt-pct MM-bal. Ni | 1.3 | 0.7 | 32 |
| 20 wt-pct MM-bal. Ni | 20.1 | 7.0 | 65 |
| 30 wt-pct MM-bal. Ni | 30.0 | 23.1 | 150 |
| 40 wt-pct MM-bal. Ni | 35.5 | 25.3 | 111 |
| 50 wt-pct MM-bal. Ni | 37.2 | 13.8 | 128 |
| 60 wt-pct MM-bal. Ni | 27.0 | 18.8 | — |
| 70 wt-pct MM-bal. Ni | 21.0 | 19.2 | — |
| 80 wt-pct MM-bal. Ni | 19.2 | 14.6 | — |

While none of the prepared catalysts approached the BET surface area displayed by the commercial catalyst, all compositions containing 30 wt-pct or more MM displayed equal or substantially higher active surface areas. All of the catalysts tested far exceeded the commercial catalyst in specific activity; the best being more than ten times as active as the commercial catalyst.

EXAMPLE 4

An alloy containing 32.3 wt-pct cerium and 67.7 wt-pct nickel was prepared by arc melting the constituents on a water cooled copper hearth in a helium atmosphere. The cooled alloy was ground to −20 +80 mesh and loaded ino a stainless steel tube reactor. Reactor temperature was then raised to 400° C. under an atmosphere of flowing helium. Thereafter, helium flow was stopped and a gas mixture containing 75% hydrogen and 25% carbon monoxide was admitted to the reactor at 10 atmospheres pressure and allowed to flow at a space velocity of 1000 hr$^{-1}$ for 17 hours. The temperature was then decreased to 200° C. and the reaction was continued for another 27 hours. At this point, the catalyst was considered to be fully activated.

Reaction temperature was then raised to 400° C. while maintaining gas composition, flow rate and pressure as before. The exit gas was sampled, analyzed and found to contain 48 mole-pct methane, 48 mole-pct water vapor and 4 mole-pct carbon dioxide. Essentially complete reaction of the feed gas had occurred. A surface area determination showed that the catalyst had a BET surface area of 31.1 m$^2$/g and an active area of 12.3 m$^2$/g as determined by carbon monoxide adsorption.

EXAMPLE 5

An alloy conforming to the composition CeCo$_5$ was prepared as in Example 1. It was treated with a synthesis gas containing hydrogen and carbon monoxide at a temperature of 336° C. overnight. This treatment resulted in a catalyst having an active surface area of 3.4 m$^2$/g. Some carbon deposition on the catalyst was observed.

These examples illustrate preferred embodiments of the invention and demonstrate its novelty, utility and advantages as compared to the prior art. Other variations in the described techniques for preparing, activating and using the catalysts of this invention will be apparent to those skilled in the art.

We claim:

1. A method for production of methane comprising reacting carbon monoxide and hydrogen at a temperature of about 350° to 400° C. and a pressure of about 1 to 100 atmospheres in the presence of a catalyst prepared by (a) forming an alloy of a first metal selected from the group consisting of nickel, cobalt, iron and mixtures thereof with a second metal selected from the group consisting of yttrium, the rare earth metals and mixtures thereof, said first metal comprising from 5 to 95 weight percent of said alloy, (b) reacting said alloy with a gas comprising hydrogen and carbon monoxide at a temperature of about 300° to 600° C. for a time sufficient to substantially completely oxidize said second metal and (c) reacting the thus-formed catalytically active product with a gas comprising hydrogen and carbon monoxide at a temperature below about 250° C. and a pressure of about 5 to 10 atmospheres for a time sufficient to enhance its catalytic activity.

2. The method of claim 1 in which said first metal is nickel.

3. The method of claim 1 in which said first metal is cobalt.

4. The method of claim 1 in which said second metal is mischmetal.

5. The method of claim 1 in which said second metal is cerium.

* * * * *